US012622921B2

(12) United States Patent
Cunningham et al.

(10) Patent No.: US 12,622,921 B2
(45) **Date of Patent: *May 12, 2026**

(54) STABLE FORMULATIONS COMPRISING THIOTEPA

(71) Applicant: SHORLA PHARMA LTD., County Tipperary (IE)

(72) Inventors: Sharon Cunningham, County Tipperary (IE); Orlaith Ryan, County Tipperary (IE); Johannes Jan Platteeuw, Boxtel (NL)

(73) Assignee: SHORLA PHARMA LTD., County Tipperary (IE)

( * ) Notice: Subject to any disclaimer, the term of this patent is extended or adjusted under 35 U.S.C. 154(b) by 721 days.

This patent is subject to a terminal disclaimer.

(21) Appl. No.: 17/897,839

(22) Filed: Aug. 29, 2022

(65) Prior Publication Data

US 2023/0041156 A1 Feb. 9, 2023

Related U.S. Application Data

(63) Continuation-in-part of application No. PCT/IB2021/057527, filed on Aug. 16, 2021.

(60) Provisional application No. 63/310,638, filed on Feb. 16, 2022, provisional application No. 63/066,378, filed on Aug. 17, 2020.

(51) Int. Cl.

| | |
|---|---|
| ***A01N 43/00*** | (2006.01) |
| ***A01N 43/46*** | (2006.01) |
| ***A61K 9/08*** | (2006.01) |
| ***A61K 31/55*** | (2006.01) |
| ***A61K 31/675*** | (2006.01) |
| ***A61K 47/02*** | (2006.01) |
| ***A61K 47/10*** | (2017.01) |
| ***A61K 47/12*** | (2006.01) |
| ***A61K 47/18*** | (2017.01) |
| ***A61K 47/20*** | (2006.01) |
| ***A61K 47/22*** | (2006.01) |

(52) U.S. Cl.

CPC .............. *A61K 31/675* (2013.01); *A61K 9/08* (2013.01); *A61K 47/02* (2013.01); *A61K 47/10* (2013.01); *A61K 47/12* (2013.01); *A61K 47/18* (2013.01); *A61K 47/20* (2013.01); *A61K 47/22* (2013.01)

(58) Field of Classification Search

None

See application file for complete search history.

(56) References Cited

U.S. PATENT DOCUMENTS

| | | | | |
|---|---|---|---|---|
| 3,014,902 A * | 12/1961 | Nakabayashi | ............ C07F 9/02 544/111 |
| 11,260,065 B2 | 3/2022 | Kovi et al. | |
| 2012/0148595 A1 | 6/2012 | Swindell et al. | |
| 2013/0046275 A1 | 2/2013 | Holzer et al. | |
| 2014/0005148 A1 | 1/2014 | Neelakantan et al. | |
| 2020/0163979 A1 | 5/2020 | Kovi et al. | |

FOREIGN PATENT DOCUMENTS

| | | | |
|---|---|---|---|
| CN | 110840832 A | 2/2020 |
| EP | 0419890 A2 | 4/1991 |
| GB | 2144327 A | 3/1985 |
| IN | 1500/CHE/2012 A | 1/2013 |
| WO | WO-2008/128299 A1 | 10/2008 |

OTHER PUBLICATIONS

International Search Report from corresponding PCT Application No. PCT/IB2023/051366, dated Apr. 19, 2023.

Written Opinion of the International Searching Authority from corresponding PCT Application No. PCT/IB2023/051366, dated Apr. 19, 2023.

International Search Report from corresponding PCT Application No. PCT/IB2021/057527, dated Nov. 25, 2021.

Kazunari, Tanaka et al.; "Evaluation of the Exposure Risk to Thiotepa from the Preparation and Administration Process of RETHIO Injection 100mg", Iryo Yakugaku—Japanese Journal of Pharmaceutical Health Care and Sciences, vol. 46, No. 3, Mar. 10, 2020, pp. 160-169.

Kondo Eisei et al.; "Pharmacokinetics of thiotepa in high-dose regimens for autologous hematopoietic stem cell transplant in Japanese patients with pediatric tumors or adult lymphoma", Cancer Chemotherapy and Pharmacology, Springer Verlag, vol. 84, No. 4, Aug. 19, 2019, pp. 849-860.

Passagne I, et al.; O/\6-methylguanine DNA-methyltransferase (MGMT) overexpression in melanoma cells induces resistance to nitrosoureas and termozolomide but sensitizes to mitomycin C, Toxicology and Applied Pharmacology, Academic Press, vol. 211, No. 2, Mar. 1, 2006, pp. 97-105.

Xu, Q. A., et al.; "Stability of Thiotepa (Lyophilized) In 5% Dextrose Injection At 4 23 °C." Am J Health Syst Pharm. Nov. 15, 1996;53(22):2728-30.

Teicher, B. A., et al. "Acute in Vivo Resistance in High-Dose Therapy." Clin. Cancer Res., Feb. 1998;4:483,491.

Office Action from corresponding U.S. Appl. No. 17/901,284, dated Jan. 20, 2023.

* cited by examiner

*Primary Examiner* — Layla Soroush

(74) *Attorney, Agent, or Firm* — Harness, Dickey & Pierce, P.L.C.

(57) ABSTRACT

The present disclosure provides pharmaceutical compositions comprising thiotepa and one selected from PEG, such as PEG400 or PEG600, and DMSO, and optionally water or an aqueous saline solution and thiosulfate. The composition is free or substantially free of impurities. Also provided is a method for treating cancer in a subject, or myeloablation prior to bone marrow transplantation using the composition. A method for enhancing the stability of a thiotepa formulation is also contemplated.

23 Claims, 1 Drawing Sheet

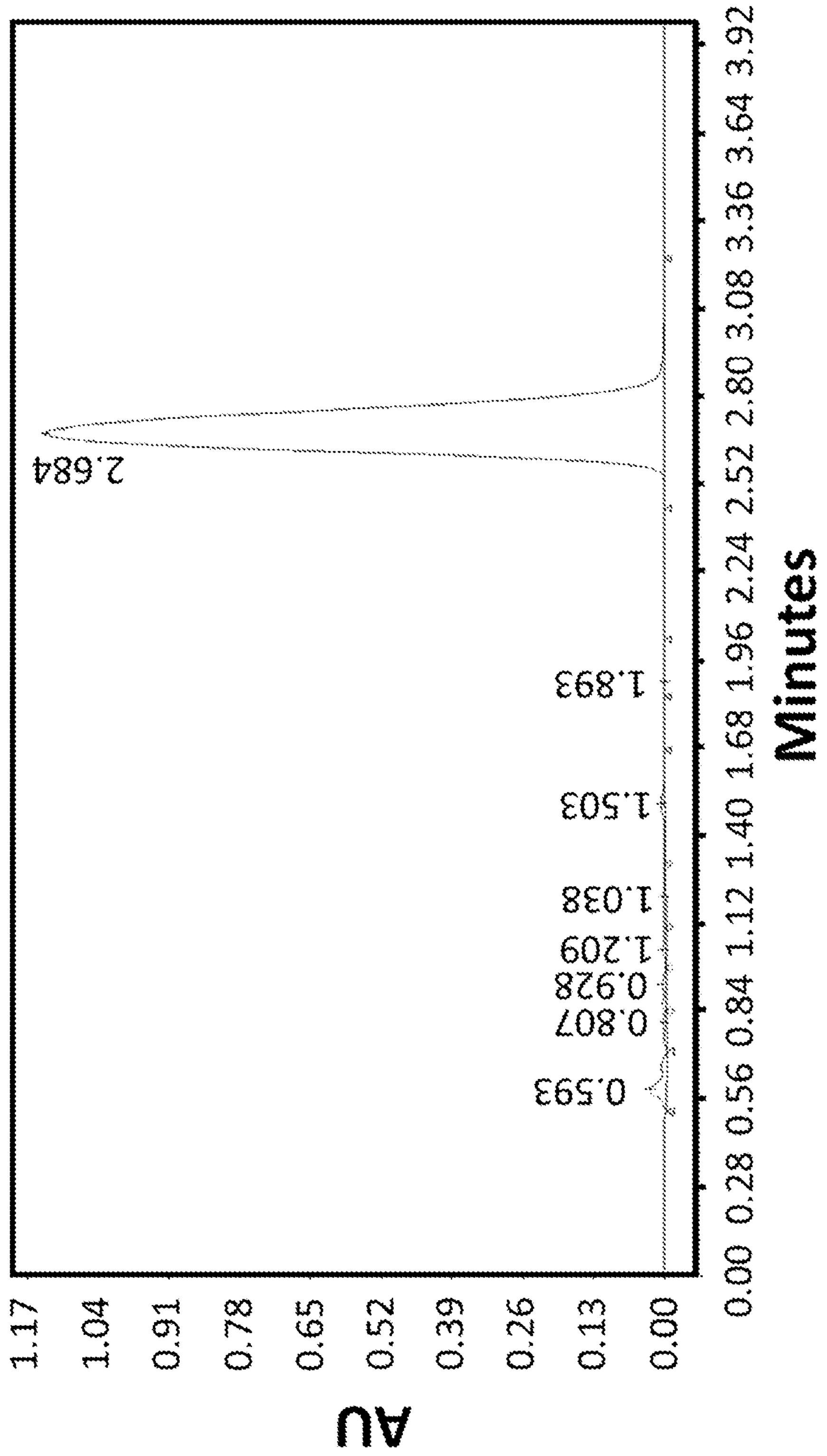
AU
1.17
1.04
0.91
0.78
0.65
0.52
0.39
0.26
0.13
0.00
Minutes
0.00
0.28
0.56
0.84
1.12
1.40
1.68
1.96
2.24
2.52
2.80
3.08
3.36
3.64
3.92
0.593
0.807
0.928
1.209
1.038
1.503
1.893
2.684

STABLE FORMULATIONS COMPRISING THIOTEPA

CROSS-REFERENCE TO RELATED APPLICATIONS

This application is a continuation in part of PCT Application PCT/IB2021/057527, filed on Aug. 16, 2021, which claims the benefit of U.S. Patent Application No. 63/066,378, filed on Aug. 17, 2020. This application also claims priority to U.S. Patent Application No. 63/310,638, filed on Feb. 16, 2022. The entire disclosure of both applications identified in this paragraph are incorporated herein by reference.

FIELD

The present disclosure relates to compositions comprising thiotepa and methods for using the same for treating a disease in a subject.

BACKGROUND

Thiotepa is a nitrogen mustard alkylating agent with antitumor properties. It is indicated for treating adenocarcinoma of the breast, superficial papillary carcinoma of the urinary bladder, and adult and pediatric hematological diseases (e.g., Hodgkin's disease or leukemia). Thiotepa is also indicated for controlling intracavitary effusions secondary to diffuse or localized neoplastic disease of serosal cavities. Thiotepa is also used as a conditioning treatment prior to allogeneic or autologous hematopoietic progenitor cell transplantation or for use in palliation of neoplastic diseases.

Thiotepa is generally unstable in aqueous solutions, which leads to the generation of impurities and/or thiotepa degradation products following storage. The aqueous instability renders ready-to-use liquid dosage forms of thiotepa difficult to store.

It is typically available as a freeze-dried product (15 mg to 100 mg) without excipients to be reconstituted to a concentration of 10 mg/mL in sterile water for injection. When provided intravenously, thiotepa can be provided as a 2-4 hour infusion at doses ranging from 3.24-14 mg/kg/day for a cumulative dose of 1050 mg/$m^2$ (42 mg/kg) to treat solid tumors.

US 2014/0005148 describes non-aqueous formulations of nitrogen mustards, including thiotepa. Nitrogen mustards are susceptible to nucleophilic attack by water and other aqueous solvents, such as ethanol, thereby degrading the nitrogen mustard into degradation products.

EP 0 419 890 reports lyophilized and water-free thiotepa compositions comprising polyethylene glycol (PEG). This reference reports that thiotepa reconstituted in water should be used within five days because reconstituted thiotepa stored longer than five days show a substantial loss of potency.

US 2020/0163979 describes pharmaceutically acceptable, injectable liquid formulations comprising thiotepa comprising at least one solvent or co-solvent, such as ethanol. The ethanol-comprising compositions are reported to have at least 90% purity of thiotepa following storage at 25° C./60% relative humidity after seven days.

SUMMARY

This section provides a general summary of disclosure and is not a comprehensive disclosure of its full scope or all of its features.

The present disclosure relates to compositions comprising thiotepa, PEG or DMSO, and water or an aqueous saline solution. The disclosed compositions are stable and may be suitable for injection. In an embodiment, the thiotepa formulation can be administered for the treatment of a disease, particularly, cancer, or myeloablation prior to bone marrow transplantation.

In an embodiment, the thiotepa composition comprises PEG such as PEG400 or PEG600. In another embodiment, the composition comprises DMSO.

In an alternative embodiment, the composition is a waterless composition comprising thiotepa and a solvent, such as DMSO, PEG400, PEG600, DMA, and NMP, wherein the composition is free or substantially free of impurities.

In an embodiment, the composition further comprises thiosulfate.

In an embodiment, there is provided a method for treating cancer in a subject, the method comprising injection administration of a composition comprising thiotepa, PEG or DMSO, and, optionally, water or an aqueous saline solution. In a further embodiment, the PEG is PEG400 or PEG600. In a particular embodiment, the administered composition further comprises thiosulfate.

In another embodiment, there is provided a method for myeloablation of a subject prior to bone marrow transplantation comprising administration of the thiotepa composition.

In another embodiment, there is provided a method for enhancing the stability of a thiotepa preparation.

BRIEF DESCRIPTION OF THE DRAWINGS

The drawings described herein are for illustrative purposes only of selected embodiments and not all possible implementations and are not intended to limit the scope of the present disclosure.

FIG. 1 shows chromatogram of a thiotepa composition of Example 1.

DETAILED DESCRIPTION

The following description is merely exemplary in nature and is not intended to limit the present disclosure, application, or uses.

The term "thiotepa" refers to the chemical compound N,N',N"-triethylenethiophosphoramide, and is also known by the trade names of Tepadina® or Thioplex®.

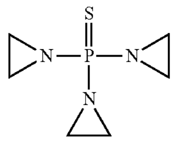 [SMILES: S=P(N1CC1)(N1CC1)N1CC1]

Unless otherwise noted, thiotepa includes the compound itself and pharmaceutically acceptable salts thereof.

The term "non-aqueous" refers to compositions (e.g., solutions, liquids, or suspensions) which are free of or essentially free of water.

The term "subject" refers to an animal that can receive administration of the thiotepa composition. In some embodiments, the subject is human. In particular embodiments, the subject has, or is thought to have cancer. In another embodiment, the subject is in need of myeloablation or lymphodepletion prior to bone marrow transplantation or other therapy requiring a conditioning regimen. In another embodiment, the subject is in need of gene therapy.

The term "cancer" includes, but is not exclusive of, bladder cancer, malignant meningeal neoplasm, breast cancer, ovarian cancer, hematological malignancies, lymphoma, brain metastases, and leptomeningeal metastasis.

The term "injection" refers to a method of administration where the composition is administered to the body via needle. In an embodiment, the injection is selected from the group consisting of subcutaneous injection, intramuscular injection, intravenous injection, infusion, intraperitoneal injection, intrapleural injection, intrapericardial injection, intrathecal injection, intra-arterial injection, intravesical injection, and intralesional injection. The injection can be a single injection, including an acute injection or a continuous injection. The injection can be delivered over a number of days.

The term "substantially free" refers to the amount of a component that is not intended to be present in a composition but still may be present due to manufacturing procedures and/or post-manufacturing degradation products. As used herein, the compositions described below may be substantially free of impurities, including but not limited to formic acid, acetic acid, formaldehyde, acetaldehyde, and peroxide. In some embodiments, a composition may be substantially free of impurities when it is processed and/or refined beyond what is conventional in the art. For example, PEG400 may undergo additional processing and/or refining and may be called "super refined, such as Super Refined™ PEG400 offered by Croda Health Care and EMPROVE® PEG offered by Sigma.

In some embodiments, a composition is substantially free of an impurity, when the impurity is present in the composition in an amount of less than about 150 ppm. In other embodiments, a composition substantially free of an impurity comprises the impurity in an amount of less than about 100 ppm, less than about 95 ppm, less than about 90 ppm, less than about 85 ppm, less than about 80 ppm, less than about 75 ppm, less than about 70 ppm, less than about 65 ppm, less than about 60 ppm, less than about 55 ppm, less than about 50 ppm, less than about 45 ppm, less than about 40 ppm, less than about 35 ppm, less than about 30 ppm, less than about 25 ppm, less than about 20 ppm, less than about 15 ppm, less than about 10 ppm, less than about 5 ppm, or less than about 1 ppm. Alternatively, the amount of an impurity in the composition may be expressed as a range, for example between about 1 and about 150 ppm, between about 1 and about 100 ppm, between about 1 and about 95 ppm, between about 1 and about 80 ppm, between about 1 and about 75 ppm, between about 1 and about 70 ppm, between about 1 and about 65 ppm, between about 1 and about 60 ppm, between about 1 and about 55 ppm, between about 1 and about 50 ppm, between about 1 and about 45 ppm, between about 1 and about 40 ppm, between about 1 and about 35 ppm, between about 1 and about 30 ppm, between about 1 and about 25 ppm, between about 1 and about 20 ppm, between about 1 and about 15 ppm, between about 1 and about 10 ppm, between about 1 and about 5 ppm, or between about 1 and about 3 ppm.

A composition is substantially free of an impurity, when concentration of the component is described as a percentage of the composition. In this manner, a composition substantially free of an impurity may comprise the impurity in an amount of less than about 0.015%, less than about 0.01%, less than about 0.0095%, less than about 0.009% less than about 0.0085%, less than about 0.008%, less than about 0.0075%, less than about 0.007%, less than about 0.0065%, less than about 0.006%, less than about 0.0055%, less than about 0.005%, less than about 0.0045%, less than about 0.004%, less than about 0.0035%, less than about 0.003%, less than about 0.0025%, less than about 0.002%, less than about 0.0015%, less than about 0.001%, less than about 0.0005%, or less than about 0.0001%. Alternatively, the amount of an impurity, in the composition may be expressed as a range of percentages, for example between about 0.001% and about 0.015%, between about 0.0001% and about 0.01%, between about 0.0001% and about 0.0095%, between about 0.0001% and about 0.009%, between about 0.0001% and about 0.0085%, between about 0.0001% and about 0.008%, between about 0.0001% and about 0.0075%, between about 0.0001% and about 0.007%, between about 0.0001% and about 0.0065%, between about 0.0001% and about 0.006%, between about 0.0001% and about 0.0055%, between about 0.0001% and about 0.005%, between about 0.0001% and about 0.0045%, between about 0.0001% and about 0.004%, between about 0.0001% and about 0.0035%, between about 0.0001% and about 0.003%, between about 0.0001% and about 0.0025%, between 0.0001% and about 0.002%, between 0.0001% and about 0.0015%, between 0.0001% and about 0.001%, or between 0.0001% and about 0.0005%.

The term "impurity" or "impurities" refers to a substance that is other than the components specifically identified and included in a composition of the present disclosure. In some embodiments, the impurity is one or more selected from the group consisting of formic acid, acetic acid, formaldehyde, acetaldehyde, and peroxide.

The term "peroxide value" refers to the concentration of hydroperoxides, which are molecules having a peroxide (—O—O—H) moiety (e.g., $H_2O_2$). Peroxide value is typically measured as milliequivalents of active $O_2$ per kg of fat matter (mEq $O_2$/kg fat).

The term "aqueous saline solution" refers to a water-based solution comprising one or more salts and/or sugars, such as sodium chloride, sodium lactate, sodium acetate, potassium chloride, calcium chloride, and dextrose. Conventional saline solutions include normal saline (0.90% w/v NaCl, 308 mOsm/L), Ringer's lactate solution, acetated Ringer's solution, and intravenous sugar solutions (e.g., saline solutions that further comprise a sugar such as dextrose).

Compositions

The present disclosure provides a composition comprising thiotepa or its derivative, such as a metabolite, and one or more excipients. Such compositions include pharmaceutical compositions comprising thiotepa, PEG or DMSO, and, optionally, water or an aqueous saline solution. Thiotepa is the active ingredient of the formulation, and its amount can be adjusted as needed. Generally, all known/approved amounts of thiotepa can be used with the formulation. In an embodiment, the thiotepa is present in an amount of about 1 to about 100 mg/mL. In a further embodiment, the thiotepa is present in an amount of about 5 to about 50 mg. In a particular embodiment, the thiotepa is present at a concentration of about 10 mg/m L.

In an embodiment when water or an aqueous saline solution is present, the water or an aqueous saline solution is present in an amount up to about 40% by weight. In another embodiment, the water or an aqueous saline solution is present in an amount of about 1%, about 2%, about 3%, about 4%, about 5%, about 6%, about 7%, about 8%, about 9%, about 10%, about 11%, about 12%, about 13%, about 14%, about 15%, about 20%, about 25%, or about 30% by weight. In a particular embodiment, the water or an aqueous saline solution is present in an amount of about 10% by weight. In some embodiments, the water is distilled, purified, or ultrapurified. In another embodiment, the aqueous saline solution may include saline or a phosphate buffer to prepare an isotonic solution. Alternatively, the composition may be free or substantially free of water or an aqueous saline solution.

The compositions described herein are free or substantially free of impurities, including, but not limited to, formic acid, acetic acid, formaldehyde, acetaldehyde, and peroxides. The compositions may comprise formic acid in an amount of less than about 150 ppm, less than about 100 ppm, less than about 35 ppm, less than about 30 ppm, less than about 25 ppm, less than about 20 ppm, less than about 15 ppm, less than about 10 ppm, less than about 5 ppm, or less than about 1 ppm. Alternatively, the formic acid may be present in a range, such as between about 1 and about 150 ppm, between about 1 and 100 ppm, between about 1 and about 35 ppm, about 1 and about 30 ppm, between about 1 and about 25 ppm, between about 1 and about 20 ppm, between about 1 and about 15 ppm, between about 1 and about 10 ppm, between about 1 and about 5 ppm, or between about 1 and about 3 ppm.

The compositions may comprise acetic acid, formaldehyde, acetaldehyde, and peroxides each in an amount of less than about 35 ppm, less than about 30 ppm, less than about 25 ppm, less than about 20 ppm, less than about 15 ppm, less than about 10 ppm, less than about 5 ppm, or less than about 1 ppm. Alternatively, the acetic acid, formaldehyde, acetaldehyde, and peroxides each may be present in a range, such as between about 1 and about 35 ppm, about 1 and about 30 ppm, between about 1 and about 25 ppm, between about 1 and about 20 ppm, between about 1 and about 15 ppm, between about 1 and about 10 ppm, between about 1 and about 5 ppm, or between about 1 and about 3 ppm The compositions described herein may have a peroxide value of less than about 2.0, less than about 1.5, less than about 1.0, less than about 0.5, or less than about 0.1. In a specific embodiment, when the excipient is PEG400, the peroxide value is less than about 1.0, preferably less than about 0.5.

Where more than one impurity is present, such as two or more of formic acid, acetic acid, formaldehyde, acetaldehyde, and peroxide, the composition may be substantially free of one or more of each impurity. For example, the composition may be substantially free of formic acid but not substantially free of peroxides. Moreover, where two or more impurities are present, the overall composition may be considered substantially free of each individual impurity where the impurities are present at different levels. For example. the composition may be considered substantially free of impurities when it comprises less than about 150 ppm formic acid, less than 15 ppm acetic acid, less than 15 ppm formaldehyde, less than 15 ppm acetaldehyde, less than 35 ppm peroxides, or a combination thereof. In another example the composition may comprise less than about 150 ppm formic acid, less than 15 ppm acetic acid, less than 15 ppm formaldehyde, less than 15 ppm acetaldehyde, and less than 35 ppm peroxides.

In an embodiment, the composition comprises PEG in an amount of between about 80% to about 100%. In another embodiment, the PEG may be a PEG between PEG200 and PEG400. In a particular embodiment, the PEG is selected from PEG400 and PEG 600. In a particular embodiment, the composition comprises Super Refined™ PEG400 (from Croda) or EMPROVE® PEG400 (from Merck).

In an alternate embodiment, the composition comprises dimethyl sulfoxide (DMSO) in an amount between about 90% to about 100%.

In another embodiment, the thiotepa composition may further comprise thiosulfate. In a particular embodiment, the thiosulfate is present in an amount between about 0.01% and about 1.0%, by weight. In still further embodiments, the thiosulfate may be present in an amount of about 0.1%, by weight.

The thiotepa composition can further comprise additional excipients and non-limiting examples of such excipients include buffers, antioxidants, and/or osmotic agents. In some embodiments, the antioxidant includes ascorbic acid, tocopherols, methionine (such as L-methionine), metabisulphite, propyl gallate, butylated hydroxyanasole, butylated hydroxytoluene, meglumine, thiosulphate salts. More preferred antioxidants are propyl gallate, thiosulphate salts, preferably sodium thiosulphate, and tocopherols, preferably α-tocopherols, more preferably α-tocopherol-PEG-succinate. α-tocopherol-PEG-succinate is a commercially available conjugate of α-tocopherol with PEG1000, and has high solubility in short PEGs. Most preferred antioxidants are thiosulphate salts, preferably sodium thiosulphate, and tocopherols, preferably α-tocopherols, more preferably α-tocopherol-PEG-succinate. In preferred embodiments is provided the composition according to the invention, further comprising an antioxidant such as a thiosulphate salt, propyl gallate, or a tocopherol. In more preferred embodiments is provided the composition according to the invention, further comprising an antioxidant selected from thiosulphate salt and/or a tocopherol. In most preferred embodiments is provided the composition according to the invention, further comprising an antioxidant selected from sodium thiosulphate and/or an α-tocopherol, preferably α-tocopherol-PEG-succinate In a particular embodiment, the composition comprises about 1 to about 100 mg/mL thiotepa, PEG or DMSO, and, optionally, up to about 20% water or an aqueous saline solution, by weight. If PEG is used, the PEG can be either PEG400 or PEG600. The composition may further comprise thiosulfate. Specific embodiments of the thiotepa composition are exemplified in Table 1.

TABLE 1

Thiotepa-containing formulations

| Component | Example 1 | 2 | 3 | 4 | 5 | 6 |
|---|---|---|---|---|---|---|
| Thiotepa (mg) | 100 | 100 | 100 | 100 | 100 | 100 |
| PEG400 | ✓ | ✓ | | | | |
| PEG600 | | | ✓ | ✓ | | |
| DMSO | | | | | ✓ | ✓ |
| Water (% by weight) | 10 | 10 | 10 | 10 | 10 | 10 |
| Thiosulfate (%) | | 0.1 | | 0.1 | | 0.1 |
| Total volume | 10 mL | | | | | |

In another embodiment, the thiotepa composition is in the form of a solution, suspension, or liquid. In a further embodiment, the thiotepa composition is an aqueous solution. In some embodiments, the compositions are in the form of a parenteral formulation suitable for injection.

In an alternative embodiment, the thiotepa is formulated in waterless compositions. In an embodiment, the waterless thiotepa composition comprises thiotepa and a solvent selected from the group consisting of DMSO, PEG400, PEG600, dimethylacetamide (DMA), and n-methyl-2-pyrrolidone (NMP). In another embodiment, the waterless thiotepa composition further comprises an antioxidant (such as tocopherol) and/or an organic base (such as Tris base). In a particular embodiment, the thiotepa composition comprises about 1 to about 100 mg/mL thiotepa, and DMSO, PEG400, PEG600, DMA, or NMP. Specific embodiments of the waterless thiotepa compositions are in Table 2.

TABLE 2

Waterless thiotepa-containing formulations

| | Example | | | | | | | | | |
|---|---|---|---|---|---|---|---|---|---|---|
| Component | 7 | 8 | 9 | 10 | 11 | 12 | 13 | 14 | 15 | 16 |
| Thiotepa (mg) | 100 | 100 | 100 | 100 | 100 | 100 | 100 | 100 | 100 | 100 |
| PEG400 | ✓ | ✓ | | | | | | | | |
| PEG600 | | | ✓ | ✓ | | | | | | |
| DMSO | | | | | ✓ | ✓ | | | | |
| DMA | | | | | | | ✓ | ✓ | | |
| NMP | | | | | | | | | ✓ | ✓ |
| Tocopherol | | ✓ | | ✓ | | ✓ | | ✓ | | ✓ |
| Tris Base | | ✓ | | ✓ | | ✓ | | ✓ | | ✓ |
| Total volume | | | | | | 10 mL | | | | |

Exemplary compositions substantially free of impurities are shown in Table 3 below. The compositions of Table 3 may be diluted with water or an aqueous saline solution (e.g., a 0.9% saline solution) prior to administration to a subject.

TABLE 3

Thiotepa-containing formulations substantially free of impurities

| | Example | | |
|---|---|---|---|
| Component | 17 | 18 | 19 |
| Thiotepa | 10 mg/mL | 10 mg/mL | 10 mg/mL |
| PEG400 | 99 wt % | — | — |
| PEG600 | — | 99 wt % | — |
| DMSO | — | — | 99 wt % |
| Formic acid | <150 ppm | <150 ppm | <150 ppm |
| Acetic acid | <15 ppm | <15 ppm | <15 ppm |
| Formaldehyde | <15 ppm | <15 ppm | <15 ppm |
| Acetaldehyde | <15 ppm | <15 ppm | <15 ppm |
| Peroxides | <35 ppm | <35 ppm | <35 ppm |
| Peroxide value | <0.5 mEq $O_2$/kg | <0.5 mEq $O_2$/kg | <0.5 mEq $O_2$/kg |

The compositions of Table 3 may be diluted with water or an aqueous saline solution (e.g., a 0.9% saline solution) prior to administration to a subject. The amount of water or aqueous saline solution used to dilute the waterless thiotepa compositions is not particularly limited and can be adjusted to accommodate the particular subject. Exemplary compositions comprising water which are substantially free of impurities are shown in Table 4 below.

TABLE 4

Thiotepa-containing formulations comprising water substantially free of impurities

| | Example | | |
|---|---|---|---|
| Component | 20 | 21 | 22 |
| Thiotepa | 10 mg/mL | 10 mg/mL | 10 mg/mL |
| Water | 10 wt % | 20 wt % | 10 wt % |
| PEG400 | 89 wt % | — | — |
| PEG600 | — | 79 wt % | — |
| DMSO | — | — | 89 wt % |
| Formic acid | <150 ppm | <150 ppm | <150 ppm |
| Acetic acid | <15 ppm | <15 ppm | <15 ppm |
| Formaldehyde | <15 ppm | <15 ppm | <15 ppm |

TABLE 4-continued

Thiotepa-containing formulations comprising water substantially free of impurities

| Component | Example 20 | Example 21 | Example 22 |
|---|---|---|---|
| Acetaldehyde | <15 ppm | <15 ppm | <15 ppm |
| Peroxides | <35 ppm | <35 ppm | <35 ppm |
| Peroxide value | <0.5 mEq $O_2$/kg | <0.5 mEq $O_2$/kg | <0.5 mEq $O_2$/kg |

The composition of the present disclosure is to address, among other things, stability issues of thiotepa in an aqueous solution. Thiotepa is known to have stability issues in aqueous solutions, such as generation of impurities and degradation of the active ingredient during storage. The aqueous instability renders ready-to-use liquid dosage forms of thiotepa difficult to store. The stable thiotepa composition of the present disclosure is suitable for a ready-to-use liquid dosage drug product. In an embodiment, the thiotepa composition is stable at room temperature (e.g., 21-25° C.) or under refrigeration (e.g., 4-5° C.) for one month, two months, three months, or longer in the dark. In another embodiment, the thiotepa is stable for up to six months at room temperature (50% relative humidity) or under refrigeration. In a particular embodiment, the thiotepa composition is stored for a period of time, such as for 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, or 3 years.

Methods of Treatment

The present disclosure provides various methods of using the thiotepa composition for the treatment of disease(s) such as cancer. In an embodiment, the thiotepa composition is administered to a subject to treat cancer, wherein the subject is in need of such treatment. Various cancers can be treated by the composition and in some embodiments, the cancer is selected from the group consisting of bladder cancer, malignant meningeal neoplasm, breast cancer, and ovarian cancer. In some other particular embodiments, the method is used for treating adenocarcinoma of the breast, controlling intracavitary effusions secondary to diffuse or localized, neoplastic diseases of various serosal cavities, and/or treating superficial papillary carcinoma of the urinary bladder. In an embodiment, the composition is used in combination with one or more chemotherapeutic agents for adult and pediatric subjects suffering from hematological diseases such as Hodgkin's disease and leukemia.

The thiotepa composition is administered to provide a therapeutically effective dose to achieve the goal or goals of the therapy. In some embodiments, the therapeutically effective amount is sufficient to treat cancer. In a particular embodiment, the therapeutically effective amount is between about 300 mg and about 700 mg. If a patient requires more than 850 mg thiotepa, the drug may be administered over two or more doses in a day. In another embodiment, the therapeutically effective amount of thiotepa is about between about 4 and about 20 mg/kg body weight. In an alternative embodiment, the therapeutically effective amount is between about 120 and about 300 $mg/m^2$. The thiotepa can be administered in a single day over the course of multiple days, such as over the course of between 1 and 5 days, in particular between 1 and 2 days.

The thiotepa composition therapy can be combined with various cancer treatments known in the art. In an embodiment, the thiotepa composition is administered to the subject in conjunction with radiotherapy. In still another embodiment, the thiotepa composition is administered before, after, or concurrently with an additional chemotherapeutic agent. For the treatment of breast cancer or ovarian cancer, the therapeutically effective dose may be between about 20 mg and about 40 mg administered every 1 to 4 weeks.

In some embodiments, a therapeutically effective amount of thiotepa is administered to induce myeloablation prior to bone marrow transplantation. In a particular embodiment, the therapeutically effective amount of thiotepa is between 300 mg and 700 mg. In another embodiment, the therapeutically effective amount of thiotepa for myeloablation prior to bone marrow transplantation is provided over 1 to 5 days, or over 1 to 2 days. The total amount of thiotepa delivered over the course of treatment for myeloablation prior to bone marrow transplantation may be about 850 mg or more.

Method of Enhancing Stability

In an embodiment is provided a method for enhancing the stability of a thiotepa formulation. In an embodiment, the method comprises the steps of: combining thiotepa and an excipient, wherein the excipient is PEG or DMSO; and homogenizing the combination. In some embodiments, the thiotepa concentration of the thiotepa in formulation following homogenization is between about 1 and about 100 mg/mL with the excipient accounting for the remainder of the composition. In some embodiments, the composition may further comprise water or an aqueous saline solution between about 1% and about 20%, by weight of the composition. In a particular embodiment, the thiotepa is present at about 10 mg/mL and, when present, the water or aqueous saline solution is present at about 10% or 20%, by weight. In a particular embodiment, the PEG is PEG400 or PEG600. In a specific embodiment, the thiotepa formulation with enhanced stability consists of 10 mg/mL thiotepa in PEG 400. In a further specific embodiment, the composition may further comprise 10% water or an aqueous saline solution, by weight. In a specific embodiment, the thiotepa formulation with enhanced stability consists of 10 mg/mL thiotepa and PEG 600. In a further specific embodiment, the composition may further comprise 20% water or an aqueous saline solution, by weight. In a specific embodiment, the thiotepa formulation with enhanced stability consists of 10 mg/mL thiotepa and DMSO. In a further specific embodiment, the composition may further comprise 10% water or an aqueous saline solution, by weight. In yet another embodiment, the formulation further comprises thiosulfate.

Further embodiments include:

1. A composition comprising thiotepa, water or an aqueous saline solution, and an excipient, wherein the excipient is polyethylene glycol (PEG) or dimethylsulfoxide (DMSO), wherein the thiotepa is present in an amount between about 1 and about 100 mg/mL, wherein the water or an aqueous saline solution is present in about up to about 40%, wherein the composition is substantially free of an impurity, and wherein the impurity is one or more selected from the group consisting of formic acid, acetic acid, formaldehyde, acetaldehyde, and peroxide.

2. The composition of paragraph 1, wherein the thiotepa is present in an amount between about 1 and about 10 mg/mL.

3. The composition of paragraphs 1 or 2, wherein the excipient is PEG400 or PEG600.

4. The composition of paragraphs 1 or 2, wherein the excipient is DMSO.

5. The composition of any one of paragraphs 1-4, wherein the water or aqueous saline solution is present in an amount selected from the group consisting of up to about 30%, up to about 25%, up to about 20%, up to about 15%, up to about 10%, and up to about 5%.

6. The composition of paragraph 5, wherein the water or aqueous saline solution is present in an amount of up to about 10%.

7. The composition of any one of paragraphs 1-6, wherein the impurity is present in an amount selected from the group consisting of less than about 150 ppm, less than about 100 ppm, less than about 35 ppm, less than about 30 ppm, less than about 25 ppm, less than about 20 ppm, less than about 15 ppm, less than about 10 ppm, and less than about 5 ppm.

8. The composition of paragraphs 1-7, wherein the impurity is present in an amount selected from the group consisting of between about 1 and about 150 ppm, between about 1 and 100 ppm, between about 1 and about 35 ppm, between 1 and about 30 ppm, between 1 and about 25 ppm, between 1 and about 20 ppm, between 1 and about 15 ppm, between 1 and about 10 ppm, and between 1 and about 5 ppm.

9. The composition of any one of paragraphs 1-8, wherein the impurity is one or more of: less than about 150 ppm formic acid; less than about 15 ppm acetic acid, less than about 15 ppm formaldehyde; less than about 15 ppm acetaldehyde; or less than about 35 ppm peroxide.

10. The composition of any one of paragraphs 1-8, wherein the impurity comprises less than about 150 ppm formic acid; less than about 15 ppm acetic acid, less than about 15 ppm formaldehyde; less than about 15 ppm acetaldehyde; and less than about 35 ppm peroxide.

11. The composition of any one of paragraphs 1-10, further comprising thiosulfate.

12. The composition of paragraph 11, wherein the thiosulfate is present in an amount of about 0.01% to about 1.0%.

13. The composition of paragraph 11 or 12, wherein the thiosulfate is present in an amount of about 0.1%.

14. The composition of paragraph 1, which consists of thiotepa, PEG400, water or aqueous saline solution, and less than about 150 ppm formic acid; less than about 15 ppm acetic acid, less than about 15 ppm formaldehyde; less than about 15 ppm acetaldehyde; and less than about 35 ppm peroxide.

15. The composition of paragraph 14, which comprises about 10 mg/mL thiotepa and about 10% water or aqueous saline solution, by weight.

16. The composition of paragraph 1, which consists of thiotepa, PEG600, water or aqueous saline solution and less than about 150 ppm formic acid; less than about 15 ppm acetic acid, less than about 15 ppm formaldehyde; less than about 15 ppm acetaldehyde; and less than about 35 ppm peroxide.

17. The composition of paragraph 16, which comprises about 10 mg/mL thiotepa and about 20% water or aqueous saline solution, by weight.

18. The composition of paragraph 1, which consists of thiotepa, DMSO, water or aqueous saline solution, and less than about 150 ppm formic acid; less than about 15 ppm acetic acid, less than about 15 ppm formaldehyde; less than about 15 ppm acetaldehyde; and less than about 35 ppm peroxide.

19. The composition of paragraph 18, which comprises about 10 mg/mL thiotepa and about 10% water or aqueous saline solution, by weight.

20. The composition of any one of paragraphs 1-19, further comprising tocopherol.

21. The composition of paragraph 1, wherein the excipient is PEG400 and the composition has a peroxide value of less than about 1.0 mEq $O_2$/kg fat.

22. The composition of paragraph 21, wherein the peroxide value is less than about 0.5 mEq $O_2$/kg fat.

23. A waterless composition comprising thiotepa and a solvent, wherein the solvent is selected from the group consisting of dimethylsulfoxide (DMSO), polyethylene glycol 400 (PEG400), polyethylene glycol 600 (PEG600), dimethylacetamide (DMA), and N-methylpyrrolidone (NMP), and wherein the thiotepa is present in an amount between about 1 and about 100 mg/mL, wherein the composition is substantially free of an impurity, and wherein the impurity is one or more selected from the group consisting of formic acid, acetic acid, formaldehyde, acetaldehyde, and peroxide.

24. The composition of paragraph 23, wherein the impurity is present in an amount selected from the group consisting of less than about 150 ppm, less than about 100 ppm, less than about 35 ppm, less than about 30 ppm, less than about 25 ppm, less than about 20 ppm, less than about 15 ppm, less than about 10 ppm, and less than about 5 ppm.

25. The composition of paragraph 23 or 24, wherein the impurity is present in an amount selected from the group consisting of between about 1 and 150 ppm, between about 1 and 100 ppm, between about 1 and about 35 ppm, between 1 and about 30 ppm, between 1 and about 25 ppm, between 1 and about 20 ppm, between 1 and about 15 ppm, between 1 and about 10 ppm, and between 1 and about 5 ppm.

26. The composition of any one of paragraphs 23-25, wherein the impurity is one or more of: less than about 150 ppm formic acid; less than about 15 ppm acetic acid, less than about 15 ppm formaldehyde; less than about 15 ppm acetaldehyde; or less than about 35 ppm peroxide.

27. The composition of any one of paragraphs 23-26, wherein the impurity comprises less than about 150 ppm formic acid; less than about 15 ppm acetic acid, less than about 15 ppm formaldehyde; less than about 15 ppm acetaldehyde; and less than about 35 ppm peroxide.

28. The waterless composition of any one of paragraphs 23-27, further comprising an antioxidant or an organic base.

29. The waterless composition of any one of paragraphs 23-28, wherein the antioxidant is tocopherol.

30. The waterless composition of any one of paragraphs 23-29, wherein the organic base is Tris base.

31. A method for treating cancer in a subject in need thereof comprising administering to the subject the composition of any one of paragraphs 1-30.

32. The method of paragraph 31, wherein the cancer is selected from the group consisting of bladder cancer, malignant meningeal neoplasm, breast cancer, and ovarian cancer.

33. The method of paragraphs 31 or 32, wherein the composition is administered via injection.

34. The method of paragraph 33, wherein the injection is selected from the group consisting of subcutaneous injection, intramuscular injection, intravenous injection, infusion, intraperitoneal injection, intrapleural injection, intrapericardial injection, intrathecal injection, intra-arterial injection, intravesical injection, and intralesional injection.

35. The method of any one of paragraphs 31-34, comprising administering about 300 mg and about 700 mg thiotepa.

36. The method of any one of paragraphs 31-35, wherein the thiotepa is stabilized.

37. A method for myeloablation prior to bone marrow transplant in a subject in need thereof comprising administering to the subject the composition of any one of paragraphs 1-30.

38. A method for enhancing the stability of a thiotepa formulation comprising: combining thiotepa and a component selected from PEG and DMSO; and homogenizing the combination, wherein the concentration of thiotepa after the step of homogenizing is between about 1 and about 100 mg/mL, wherein the composition is substantially free of an impurity, and wherein the impurity is one or more selected from the group consisting of formic acid, acetic acid, formaldehyde, acetaldehyde, and peroxide.

39. The method of paragraph 38, wherein the concentration of thiotepa is about 10 mg/m L.

40. The method of paragraphs 38 or 39, further comprising adding water or an aqueous saline solution, wherein the water or aqueous saline solution comprises about 10% or about 20%, by weight, of the composition.

41. The method of any one of paragraphs 38-40, wherein the PEG is PEG400 or PEG600.

42. The method of any one of paragraphs 38-41, wherein the thiotepa formulation consists of 10 mg/mL thiotepa and PEG400.

43. The method of any one of paragraphs 38-41, wherein the thiotepa formulation consists of 10 mg/mL thiotepa and PEG600.

44. The method of any one of paragraphs 38-41, wherein the thiotepa formulation consists of 10 mg/mL thiotepa and DMSO.

45. The method of any one of paragraphs 38-44, further comprising adding thiosulfate to the composition.

46. The method of paragraph 45, wherein the thiosulfate comprises about 0.01% to about 10%, by weight.

47. The method of paragraph 46, wherein the thiosulfate comprises about 0.1%, by weight.

EXAMPLES

Example 1: Stability of Aqueous Thiotepa Compositions 100 mg thiotepa was weighed into an amber vessel and 10 mL PEG400, PEG600, or DMSO (as appropriate) was subsequently added to the vessel. Purified water was added to the vessel at 10% (Examples 1, 2, 5, and 6) or 20% (Examples 3 and 4) by weight. 0.1% thiosulfate (by weight) was added to Examples 2, 4, and 6. The preparations were homogenized with a magnetic stirrer and stirred overnight. The preparations were aliquoted to separate vials and stored at 5° C. or 25° C./60% relative humidity (RH).

The preparations were assayed by HPLC at 2 weeks, 1.5 months (6 weeks), 3.5 months, and 5 months. Relative standard deviation (RSD) was calculated for each sample. The total and chloroethyl impurities were also quantified by HPLC. HPLC was performed on a Waters, Xbridge shield Rp18, 75×4.6 mm, dp=2.5 μm, with a flow of 1.5 mL/min, an injection volume of 8 μL, and a run time of 12 minutes.

Tables 5 and 6 show the stability of thiotepa formulations at 5° C. and 25° C./60% RH, respectively.

TABLE 5

Thiotepa stability at 5° C. (RSD is relative standard deviation)

| | T = 0 | | t = 2 weeks | | T = 1.5 month | | t = 3.5 month | | | | t = 5 month | | | |
|---|---|---|---|---|---|---|---|---|---|---|---|---|---|---|
| Ex. | Assay (%) | RSD (%) | Assay (%) | RSD (%) | Assay (%) | RSD (%) | Assay (%) | RSD (%) | Total Impur (%) | Chloro impur (%) | Assay (%) | RSD (%) | Total Impur (%) | Chloro impur (%) |
| 1 | 101.0 | 0.61 | 107.7 | 0.76 | 103.3 | 0.15 | 109.6 | 0.16 | 0.24 | 0.00 | 108.1 | 0.65 | 0.22 | 0.00 |
| 2 | 96.3 | 0.18 | 72.4 | 0.24 | 83.3 | 0.01 | 83.3 | 0.08 | 18.00 | 0.15 | 79.1 | 0.33 | 20.22 | 0.72 |
| 3 | 107.0 | 0.00 | 110.8 | 7.43 | 104.2 | 0.48 | 109.8 | 0.35 | 0.29 | 0.00 | 113.7 | 1.44 | 0.42 | 0.05 |
| 4 | 89.5 | 0.31 | 88.9 | 3.82 | 89.3 | 1.33 | 92.3 | 0.31 | 15.96 | 0.04 | 93.1 | 0.35 | 16.83 | 0.00 |
| 5 | 101.0 | 0.27 | 99.0 | 3.68 | 100.4 | 0.52 | 99.3 | 0.34 | 0.15 | 0.00 | 100.5 | 7.19 | 0.19 | 0.00 |
| 6 | 86.4 | 0.24 | 76.6 | 1.39 | 75.4 | 0.00 | 76.0 | 3.56 | 18.84 | 1.62 | 75.3 | 1.04 | 20.21 | 0.17 |
| 7 | 95.8 | 0.15 | 67.1 | 13.1 | 87.8 | 0.30 | 86.6 | 2.83 | 16.05 | 0.09 | 86.2 | 1.20 | 15.51 | 0.00 |

TABLE 6

Thiotepa stability at 25° C./60% RH

| | T = 0 | | t = 2 weeks | | t = 1.5 month | | t = 3.5 month | | | | t = 5 month | | | |
|---|---|---|---|---|---|---|---|---|---|---|---|---|---|---|
| Ex. | Assay (%) | RSD (%) | Assay (%) | RSD (%) | Assay (%) | RSD (%) | Assay (%) | RSD (%) | Total Impur (%) | Chloro impur (%) | Assay (%) | RSD (%) | Total Impur (%) | Chloro impur (%) |
| 1 | 101.0 | 0.61 | 108.7 | 0.13 | 99.37 | 1.16 | 100.7 | 0.09 | 1.11 | 0.35 | 98.75 | 1.07 | 1.39 | 0.51 |
| 2 | 96.3 | 0.18 | 95.5 | 0.46 | 37.50 | 1.38 | 8.42 | n = 1 | 3.52 | 0.11 | | Not measured | | |
| 3 | 107.0 | 0.00 | 115.7 | 7.41 | 101.23 | 0.67 | 100.5 | n = 1 | 1.26 | 0.12 | 98.58 | 0.25 | 7.05 | 0.35 |

TABLE 6-continued

Thiotepa stability at 25° C./60% RH

| Ex. | T = 0 Assay (%) | T = 0 RSD (%) | t = 2 weeks Assay (%) | t = 2 weeks RSD (%) | t = 1.5 month Assay (%) | t = 1.5 month RSD (%) | t = 3.5 month Assay (%) | t = 3.5 month RSD (%) | t = 3.5 month Total Impur (%) | t = 3.5 month Chloro impur (%) | t = 5 month Assay (%) | t = 5 month RSD (%) | t = 5 month Total Impur (%) | t = 5 month Chloro impur (%) |
|---|---|---|---|---|---|---|---|---|---|---|---|---|---|---|
| 4 | 89.5 | 0.31 | 95.1 | 0.19 | 77.99 | 8.68 | 74.71 | 11.4 | 15.69 | 0.09 | 64.97 | 0.96 | 15.36 | 0.09 |
| 5 | 101.0 | 0.27 | 102.4 | 0.16 | 94.14 | 8.98 | 79.04 | 3.10 | 2.47 | 0.00 | 95.77 | 0.24 | 2.73 | 0.00 |
| 6 | 86.4 | 0.24 | 82.7 | 2.42 | 55.22 | 6.29 | 51.59 | 15.9 | 17.92 | 1.44 | 30.50 | 12.9 | * | 0.00 |
| 7 | 95.8 | 0.15 | 86.5 | 2.62 | 30.81 | 25.01 | 6.44 | 0.05 | 5.84 | 0.10 | 0.91 | 17.7 | * | 0.00 |

As seen in the above tables, PEG and DMSO formulations with 10% or 20% water were stable when stored at 5° C. PEG400- and PEG600-containing formulations are stable up to 5 months, at both 5° C. and 25° C./60% RH. FIG. 1 shows a chromatogram of a thiotepa composition of Example 1.

Example 2: Stability of Waterless Thiotepa Compositions 100 mg thiotepa was weighed into an amber vessel and 10 mL PEG400, PEG600, DMSO, DMA, or NMP (as appropriate) was subsequently added to the vessel. Tocopherol and Tris base was included in some formulations The preparations were homogenized with a magnetic stirrer and stirred overnight. The preparations were aliquoted to separate vials and stored at 5° C. or 25° C./60% RH.

The preparations were assayed by HPLC at 2 weeks, 1 month, and 2 months. Relative standard deviation (RSD) was calculated for each sample. The total and chloroethyl impurities were also quantified by HPLC. HPLC was performed on a Waters, Xbridge shield Rp18, 4.6×150 mm, dp=3.5 μm, with a flow of 1.0 mL/min, and an injection volume of 20 μL.

Tables 7 and 8 show the stability of thiotepa formulations at 5° C. and 25° C./60% RH, respectively.

TABLE 7

Waterless thiotepa stability at 5° C.

| Ex. | t = 0 Assay (%) | t = 0 RSD (%) | t = 0 Impur (%) | t = 2 weeks Assay (%) | t = 2 weeks RSD (%) | t = 2 weeks Impur (%) | t = 1 month Assay (%) | t = 1 month RSD (%) | t = 1 month Impur (%) | t = 2 month Assay (%) | t = 2 month RSD (%) | t = 2 month Impur (%) |
|---|---|---|---|---|---|---|---|---|---|---|---|---|
| 7 | — | — | — | 106.12 | 2.56 | 2.79 | 103.71 | 1.28 | 0.13 | 93.93 | 4.31 | 4.737 |
| 9 | — | — | — | 102.41 | 0.16 | 1.79 | 104.76 | 0.28 | 0.00 | 106.76 | 1.97 | 1.996 |
| 11 | 100.25 | 0.24 | 0.02 | 104.42 | 0.23 | 0.04 | 108.78 | 0.82 | — | 89.52 | 48.31 | 2.738 |
| 13 | 100.57 | 0.79 | — | 95.88 | 1.68 | — | 92.64 | 1.71 | — | 100.90 | 0.31 | — |
| 15 | 101.01 | 0.43 | 0.26 | 103.96 | 1.04 | — | 110.84 | 3.19 | — | 99.22 | 0.45 | 4.245 |

TABLE 8

Waterless thiotepa stability at 25° C./60% RH

| Ex. | t = 0 Assay (%) | t = 0 RSD (%) | t = 0 Impur (%) | t = 2 weeks Assay (%) | t = 2 weeks RSD (%) | t = 2 weeks Impur (%) | t = 1 month Assay (%) | t = 1 month RSD (%) | t = 1 month Impur (%) | t = 2 month Assay (%) | t = 2 month RSD (%) | t = 2 month Impur (%) |
|---|---|---|---|---|---|---|---|---|---|---|---|---|
| 7 | — | — | — | 113.52 | 0.44 | 1.26 | 100.59 | 1.48 | 2.64 | 97.42 | 2.18 | 0.812 |
| 9 | — | — | — | 116.11 | 0.06 | 0.99 | 107.20 | 0.35 | 0.07 | 106.35 | 0.65 | 0.888 |
| 11 | 100.25 | 0.24 | 0.02 | 97.80 | 4.04 | 1.26 | 100.59 | 1.48 | 2.64 | 97.42 | 2.18 | 0.812 |
| 13 | 100.57 | 0.79 | — | 96.94 | 0.98 | — | 90.73 | 0.73 | — | 103.48 | 3.26 | — |
| 15 | 101.01 | 0.43 | 0.26 | 100.58 | 0.05 | 0.23 | — | — | — | 97.33 | 1.55 | 1.314 |

Example 3: Comparison of Commercially Available PEG400

Four batches of PEG400 were obtained from three suppliers and analyzed for the amount of the following impurities: formic acid, acetic acid, formaldehyde, acetaldehyde, and peroxide. The sources and grades of the PEG400 batches are shown in Table 9 below.

TABLE 9

PEG400 batches assayed for impurities

| Code | Supplier | Catalogue No. | Batch No. | Grade/Description |
|---|---|---|---|---|
| PEG1 | Merck | 817003 | K53459103 202 | EMPROVE ® Essential Ph Eur |
| PEG2 | Merck | 807485 | S6763885 410 | PEG400 for synthesis |
| PEG3 | Croda | SR40377 | 0001747476 | Super Refined ™ PEG400-LQ-(MH) |
| PEG4 | BASF | 807485 | S8117085201 | Kollisolv ® |

All four batches of PEG400 were analyzed by liquid chromatography for each of formic acid, acetic acid, formaldehyde, acetaldehyde, and peroxide. The impurity content (measured in ppm) for each batch is shown in Table 10 below. As shown in the table, the impurity profile of commercially available PEG400 varied dramatically.

TABLE 10

Impurity content (ppm) for PEG400 batches

| Code | Formic Acid | Acetic Acid | Formaldehyde | Acetaldehyde | Peroxide |
|---|---|---|---|---|---|
| PEG1 | 145 | 13 | 3.2 | 3.0 | 3.3 |
| PEG2 | 1534 | 739 | 87 | 77 | 53 |
| PEG3 | 91 | 2.2 | 15 | 7.4 | 22 |
| PEG4 | 184 | 438 | 29 | 9.3 | 70 |

Each of the commercially available batches were combined with thiotepa to prepare a waterless composition comprising 10 mg/mL thiotepa. Each of the compositions were prepared according to Table 11 below.

TABLE 11

Tested PEG400 formulations

| Formulation | PEG400 Code | PEG400 (g) | Thiotepa (mg) |
|---|---|---|---|
| A | PEG1 | 33.54541 | 299.69 |
| B | PEG2 | 33.53255 | 299.18 |
| C | PEG3 | 27.78969 | 249.01 |
| D | PEG4 | 33.54353 | 300.32 |

100 mg thiotepa was weighed into an amber vessel with 10 mL PEG400. The preparations were homogenized with a magnetic stirrer and stirred overnight. The preparations were aliquoted to separate vials and stored at 40° C. for two weeks. The thiotepa and total impurities were quantified by HPLC. HPLC was performed on a Waters, Xbridge shield Rp18, 75×4.6 mm, dp=2.5 μm, with a flow of 1.5 mL/min, an injection volume of 8 μL, and a run time of 12 minutes. Table 12 shows the stability of thiotepa before storage and after two weeks of storage at 40° C. Table 13 shows the presence of total impurities of the formulation before storage or after two weeks of storage at 40° C.

TABLE 12

Stability of thiotepa

| Formulation | T = 0 (%) | T = 2 weeks (%) |
|---|---|---|
| A | 97.3 | 94.8 |
| B | 83.4 | 82.8 |
| C | 99.2 | 96.9 |
| D | 96.1 | 92.5 |

TABLE 13

Presence of thiotepa impurities

| Formulation | T = 0 (%) | T = 2 weeks (%) |
|---|---|---|
| A | 0.16 | 0.92 |
| B | 18.00 | 17.96 |
| C | 0.37 | 0.76 |
| D | 3.28 | 5.57 |

Tables 12 and 13 show that thiotepa is most stable with the least impurities in formulations prepared with PEG1 or PEG3, each of which contain less than 35 ppm acetic acid, formaldehyde, acetaldehyde, and peroxide, and less than 150 or 100 ppm formic acid, respectively.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for treating cancer or inducing myeloablation prior to bone marrow transplantation or controlling intracavitary effusions secondary to diffuse or localized, neoplastic diseases of various serosal cavities in a subject in need thereof comprising:

administering to the subject a composition comprising thiotepa and a solvent, wherein the solvent is selected from the group consisting of dimethylsulfoxide (DMSO), polyethylene glycol 400 (PEG400), polyethylene glycol 600 (PEG600), dimethylacetamide (DMA), and N-methylpyrrolidone (NMP), and wherein the thiotepa is present in an amount between about 1 and about 100 mg/mL, wherein the composition is substantially free of an impurity, wherein the impurity is one or more selected from the group consisting of formic acid, acetic acid, formaldehyde, acetaldehyde, and peroxide, and wherein the cancer is selected from the group consisting of bladder cancer, malignant meningeal neoplasm, breast cancer, ovarian cancer, lymphoma, and leptomeningeal metastasis.

2. The method of claim 1, wherein the impurity is present in an amount selected from the group consisting of less than about 150 ppm, less than about 100 ppm, less than about 35 ppm, less than about 30 ppm, less than about 25 ppm, less than about 20 ppm, less than about 15 ppm, less than about 10 ppm, and less than about 5 ppm.

3. The method of claim 1, wherein the composition does not comprise water.

4. The method of claim 3, wherein the composition comprises one or more of:

less than about 150 ppm formic acid;
less than about 15 ppm acetic acid;
less than about 15 ppm formaldehyde;
less than about 15 ppm acetaldehyde; or
less than about 35 ppm peroxide.

5. The method of claim 4, wherein the composition comprises:

less than about 150 ppm formic acid;
less than about 15 ppm acetic acid;
less than about 15 ppm formaldehyde;
less than about 15 ppm acetaldehyde; and
less than about 35 ppm peroxide.

6. The method of claim 5, wherein the composition comprises thiotepa and PEG400.

7. The method of claim 5, wherein the composition comprises thiotepa and PEG600.

8. The method of claim 5, wherein the composition comprises thiotepa and DMSO.

9. The method of claim 1, wherein the composition further comprises water.

10. The method of claim 9, wherein the water is present in an amount selected from the group consisting of up to about 30%, up to about 25%, up to about 20%, up to about 15%, up to about 10%, and up to about 5%.

11. The method of claim 10, wherein the composition comprises one or more of:

less than about 150 ppm formic acid;
less than about 15 ppm acetic acid;
less than about 15 ppm formaldehyde;
less than about 15 ppm acetaldehyde; or
less than about 35 ppm peroxide.

12. The method of claim 11, wherein the composition comprises:

less than about 150 ppm formic acid;
less than about 15 ppm acetic acid;
less than about 15 ppm formaldehyde;
less than about 15 ppm acetaldehyde; and
less than about 35 ppm peroxide.

13. The method of claim 12, wherein the composition comprises thiotepa and PEG400.

14. The method of claim 12, wherein the composition comprises thiotepa and PEG600.

15. The method of claim 12, wherein the composition comprises thiotepa and DMSO.

16. The method of claim 9, wherein the water is an aqueous saline solution.

17. The method of claim 1, wherein the composition further comprises thiosulfate.

18. The method of claim 17, wherein the thiosulfate is present in an amount of about 0.01% to about 1.0%.

19. The method of claim 1, wherein the composition is administered via injection which is selected from the group consisting of subcutaneous injection, intramuscular injection, intravenous injection, infusion, intraperitoneal injection, intrapleural injection, intrapericardial injection, intracavitary injection, intrathecal injection, intra-arterial injection, intravesical injection, and intralesional injection.

20. The method of claim 1, comprising administering about 300 mg to about 700 mg thiotepa.

21. A method for enhancing the stability of a thiotepa formulation comprising:

combining thiotepa, and a component selected from PEG and DMSO; and
homogenizing the combination,
wherein the concentration of thiotepa after the step of homogenizing is between about 1 and about 100 mg/mL,
wherein the formulation is substantially free of an impurity, and
wherein the impurity is one or more selected from the group consisting of formic acid, acetic acid, formaldehyde, acetaldehyde, and peroxide.

22. The method of claim 1, wherein the method reduces a risk of graft rejection, and wherein the cancer includes adenocarcinoma of the breast or ovary and superficial papillary carcinoma of the urinary bladder.

23. The method of claim 1, comprising administering about 20 mg to about 40 mg thiotepa.

* * * * *